United States Patent [19]

Veltman

[11] Patent Number: 4,756,838
[45] Date of Patent: Jul. 12, 1988

[54] PREPARATION OF DRY DIALYSATE PRODUCTS

[76] Inventor: Preston L. Veltman, 212 Old County Rd., Severna Park, Md. 21146

[21] Appl. No.: 193,125

[22] Filed: Oct. 2, 1980

Related U.S. Application Data

[63] Continuation-in-part of Ser. No. 123,355, Feb. 21, 1980, abandoned.

[51] Int. Cl.[4] .................. A61K 33/06; A61K 33/14; C09K 3/00
[52] U.S. Cl. ..................................... 252/1; 23/313 R; 210/646; 210/647; 252/363.5; 424/153
[58] Field of Search ..................... 252/1; 210/646, 647; 23/313 R; 424/153

[56] References Cited

U.S. PATENT DOCUMENTS

| | | | |
|---|---|---|---|
| 2,700,604 | 1/1955 | Knight | 252/1 X |
| 2,877,159 | 3/1959 | Lachman et al. | 23/313 R X |
| 3,339,618 | 9/1967 | Bowden et al. | 23/313 R X |
| 3,560,380 | 2/1971 | Stade | 252/1 |
| 4,202,760 | 5/1980 | Storey et al. | 210/647 |

FOREIGN PATENT DOCUMENTS

| | | | |
|---|---|---|---|
| 0003914 | 9/1979 | European Pat. Off. | 210/647 |
| 144360 | 10/1980 | German Democratic Rep. | 210/647 |

OTHER PUBLICATIONS

Chem. Abstracts, vol. 91, No. 6, pp. 4474 and 4475, Aug. 6, 1979—Abstract No. 91:44474r.
"Bicarb", Drake Willock, Subsidiary of Becton Dickinson & Co., 500 N.E. Multnomah, Suite 1300, Portland, Oreg. 97232, (1979).
Mion et al.: "Substitution of Sodium Actate for Sodium Bicarbonate in the Bath Fluid for Hemodialysis", vol. X, Trans. Am. Soc. Artif. Int. Organs, pp. 110–113, (1964).
Kirkendol et al.: "Potential Source of Fixed Base in Hemodialysate Solutions", vol. XXIII, Trans. Am. Soc. Artif. Intern. Organs, pp. 399–405, (1977).
Graefe et al.: "Less Dialysis–Induce Morbidity and Vascular Instability with Bicarbonate in Dialysate", Annals of Internal Medicine, vol. 88, No. 3, pp. 332–336, (Mar. 1978).
Campanella: "Baxter Travenol's New Bag", Barron's Jun. 2, 1980, pp. 35 and 42.

Primary Examiner—Richard D. Lovering
Attorney, Agent, or Firm—Armstrong, Nikaido, Marmelstein & Kubovcik

[57] ABSTRACT

This invention is directed to dry, free-flowing, stable readily soluble, non-caking, particulate solid products which are readily soluble in water and which are useful for preparing solutions for use in hemodialysis and peritoneal dialysis and to the preparation of these granular products.

7 Claims, 4 Drawing Sheets

PREPARATION OF DRY DIALYSATE PRODUCTS

CROSS REFERENCE TO RELATED APPLICATION

This is a continuation-in-part of application Ser. No. 123,355, filed Feb. 21, 1980 and now abandoned.

The specification of said application Ser. No. 123,355, in its entirety, is incorporated herein by reference.

BACKGROUND OF THE INVENTION

1. Field of the Invention

This invention relates to hemodialysis and peritoneal dialysis.

More particularly, this invention relates to: (a) dry, free-flowing, stable, dust-free, non-caking, granular products or compositions which are readily soluble in water and which are suitable and useful for preparing solutions for use in hemodialysers and in peritoneal dialysis and (b) to the preparation of such granular products.

2. Description of the Prior Art

Hemodialysers, which are known as "artificial kidneys" and which are also referred to as "dialysers", are used in the care of patients suffering from renal deficiencies because of disease or injury. Such devices remove waste matter (waste products of metabolism) from blood by means of a semipermeable membrane and a specially formulated solution which extracts the wast matter through the semi-permeable membrane. In hemodialysis, blood is removed from a patient's body and circulated through a dialyser to remove waste products from the blood. On the other hand, in peritoneal dialysis, a dialysis solution is injected into the patient's abdominal cavity where wastes pass through the membranes of the patient's body into the dialysis solution which is subsequently drained from the abdominal cavity.

Solutions used in hemodialysers or in peritoneal dialysis generally contain, as major components, dextrose (if required by the patient), sodium chloride and sodium acetate and/or sodium bicarbonate (the sodium acetate or sodium bicarbonate serves as an alkalizing agent), along with smaller amounts of calcium, magnesium and sometimes potassium as chlorides and other water soluble physiologically acceptable salts, such as small amounts of lactates or gluconates if required by the patient. These materials (e.g., lactates and gluconates) must not be present in amounts sufficient to precipitate calcium or magnesium ions. Potassium acetate and gluconates and lactates of sodium, potassium, magnesium or calcium, if present, also serve as alkalizing agents.

Peritoneal dialysis is described in the June 2, 1980 issue of Barrons at pages 35 and 42.

To date, commercial practice has been largely limited to supplying hemodialysis and peritoneal dialysis solutions in the form of liquid concentrates, although it has been recognized for years that a stable dry product capable of being readily and completely dissolved in water would have convenience and handling cost advantages. Such a dry product is taught by U.S. Pat. No. 3,560,380. Products described therein are made by combining a specially prepared spray-dried sodium acetate, having a moisture content of less than 0.2% by weight, with ordinary anhydrous grades of other materials to form a simple physical mixture. A further provision is that the total moisture content of the composition does not exceed 0.75%. Product stability against caking and discoloration is said to result from the low water content of the spray-dried sodium acetate. Such products have not obtained broad acceptance in the marketplace, possibly because of the small particle size of the spray-dried materials. Spray-dried sodium acetate is dusty and, consequently, has unpleasant handling characteristics.

A prior art dialysis solution based on bicarbonate is described in a bulletin entitled "SB-600 Bicarbonate Batch Formula", published by Renal Systems, Inc., 14905 28th Ave. North, Minneapolis, Minn. 55441. The precursor of said solution is provided in two parts. These are (a) a first part comprising 3.42 liters of an "acid based concentrate", and (b) a second part which is 393 g of sodium bicarbonate. The first part is diluted to slightly less than 120 liters with water, the second part (the sodium bicarbonate) is admixed in approximately one quart of water and added to the aforesaid diluted first part. The resulting mixture is diluted with water to 120 liters to form a bicarbonate based dialysis solution which will be referred to as "Solution A". Said Solution A contains:

|  | MEq/l | Eq/l |  | gms/l |
|---|---|---|---|---|
| Sodium | 140 | or 0.140 | or 0.14 × 23 | = 3.22 |
| Calcium | 3.5 | or 0.0035 | or 0.0035 × $\frac{40.08}{2}$ | = 0.0701 |
| Magnesium | 1.5 | or 0.0015 | or 0.0015 × $\frac{24.32}{2}$ | = 0.0182 |
| Chloride | 106 | or 0.106 | or 0.106 × 35.45 | = 3.7577 |
| Bicarbonate | 35 | or 0.035 | or 0.035 × 61 | = 2.1350 |
| Dextrose ($C_6H_{12}O_6$) | 250 | or 0.250 | or 0.250 × 180 | = 45.0 |

As noted supra, in the above Renal Systems SB-600 Bicarbonate Batch Formula, all constituents except the sodium bicarbonate are contained in the acid based concentrate as sodium chloride, calcium chloride, magnesium chloride and dextrose.

Other chemicals (e.g., potassium chloride), if required, are added and, if necessary, the pH is adjusted to 7.2 to 7.4 after mixing the acid based concentrate and the sodium bicarbonate but before using the resulting solution.

It should be noted that the use of sodium bicarbonate comprising dialysate solutions is complicated by the fact that calcium and magnesium ions do not remain soluble in the presence of concentrated sodium bicarbonate solutions. In the presence of water, calcium and magnesium ions tend to combine with carbonate present and readily precipitate at low concentrations. pH must be closely controlled.

In the early 1960s (Mion, C. M. et al, "Substitution of Sodium Acetate for Sodium Bicarbonate in the Bath Fluid for Hemodialysis", Trans. Am. Soc. Artif. Internal Organs 10:110, 1964), sodium acetate was instituted for sodium bicarbonate as the fixed base in hemodialysis solutions. This was done primarily because the sodium acetate containing solutions were more stable in use, whereas the sodium bicarbonate comprising solutions were less stable because of the low solubility of calcium and magnesium carbonates. It is essential that exact control of various necessary ions in the dialysis solution be obtained. The tendency for calcium and magnesium carbonates to precipitate at solution use concentrations caused the switch in 1964 from sodium bicarbonate as the fixed base to sodium acetate. This switch also made possible the use of proportioning pumps to handle dialysate concentrates.

Information is now surfacing indicating that there is "Less Dialysis-Induced Morbidity and Vascular Instability with Bicarbonate in Dialysate" (U. Graefe et al, March, 1978, Annals of Internal Medicine, Vol. 88, No. 3, pages 332-336). It is now evident that bicarbonate in a dialysate solution, rather than acetate, is better tolerated by the patient.

SUMMARY OF THE INVENTION

Sodium Acetate System

It is an object of the present invention to provide a solid system (a granular product) based on the use of sodium acetate as the alkalyzing agent which is useful for preparing a solution for use in hemodialysis or peritoneal dialysis. Said system is a dry, free-flowing, non-caking, chemically homogeneous color-stable, readily water-soluble granular product useful for preparing a hemodialysis solution or a peritoneal dialysis solution based on sodium acetate as the alkalizing agent. The product comprises an intimate admixture of sodium acetate and sodium chloride and physiologically acceptable salts of magnesium and calcium, for example, magnesium chloride and calcium chloride. If required or desired, minor amounts of lactate ions and/or gluconate ions can be present. These are usually provided as the sodium salts but can be provided as calcium or magnesium salts or as potassium salts if potassium ions are included in the granular product.

Said product is further characterized in that the granules are chemically homogeneous since each granule exists as a "micro homogeneous mixture" of discrete particles of simultaneously formed mixed small crystals or amorphous forms of components. That is to say, each product granule has substantially the same chemical composition as any other granule from the same lot. The granular product (granules) is preferably in the range of −20 to +100 mesh, and is notably dust-free and uniquely rapidly soluble in water. The low water content, absence of fines and somewhat open, i.e., porous, granular structure mitigates against bulk caking during storage and during the solution process. Further, individual components comprising the granular products of this invention do not physically separate one from the other during handling and storage as is often the case with simple mixtures.

If required or desired, a potassium salt selected from the group consisting of (a) potassium chloride, (b) potassium lactate, (c) potassium acetate, and (d) potassium gluconate can be included in the granular product. Potassium chloride is generally preferred.

The dry, non-caking, free-flowing, stable, readily soluble, dust-free granular sodium acetate system of this invention is heterogeneous in the physical sense because the individual granules are aggregates of small crystals of the individual salts constituting or comprising the granules. However, the granules are homogeneous on a particulate basis (i.e., they are chemically homogeneous) because each individual granule contains a constant portion of the individual components. Product granules are preferably about −20 mesh and +100 mesh.

Solid masses, e.g., sheets, lumps, large granules, chunks and the like of said sodium acetate-alkalyzed system of a specific run (before crushing to prepare the final granular product) are chemically homogeneous because samples taken from randomly selected portions of such masses have substantially the same chemical composition.

The granular sodium acetate system of this invention is readily soluble because a 60 g portion of said product can be completely dissolved in 140 g of water in a 400 ml beaker at about 20°-30° C. when using gentle stirring in less than three minutes. Gentle stirring as used herein means stirring with a 1-inch blade in a 400 ml beaker at about 300 RPM.

It is another object of this invention to provide a method for preparing the above-described granular product by a process characterized in that salts to be included in the granules comprising the granular product are admixed in the presence of water. Said water can be the water of hydration of at least one of said salts, or it can be liquid water which is admixed with said salts to form a partial or complete solution thereof. The water is rapidly vaporized to form a dry solid product which is crushed and sized to form product and material for recycling in the process. Each of the resulting granules is an intimate admixture of minute particles of each component, the components being the above-mentioned salts.

Sodium Bicarbonate Systems

It is also an object of the present invention to provide dry free-flowing, non-caking, color stable, readily water soluble granular products useful for preparing a hemodialysis solution or a peritoneal dialysis solution, such solution being based on sodium bicarbonate as the primary alkalizing agent.

In the sodium bicarbonate systems of this invention wherein sodium bicarbonate serves as the primary (main) alkalizing agent, the sodium bicarbonate is handled as a separate entity and only admixed with the other constituents after the complete removal of water from said other constituents.

The sodium bicarbonate systems can contain minor amounts of sodium, magnesium, calcium and potassium acetates, lactates and gluconates (or mixtures thereof) as secondary (minor) alkalyzing agents.

In the absence of water, in which materials can dissolve, calcium and magnesium salts do not react with sodium bicarbonate to form insoluble carbonates.

Two different sodium bicarbonate system accomplish this object. These are:

First Sodium Bicarbonate System

The product of the first sodium bicarbonate system consists essentially of a dry, free-flowing, non-caking, chemically homogeneous, color stable, readily water-soluble first granular product comprising an intimate admixture of sodium chloride and physiologically acceptable ionic salts of magnesium and calcium plus, if desired, a minor amount of sodium acetate, sodium lactate or sodium gluconate. Said salts of magnesium and calcium can have anions selected from the group consisting of: (i) chloride, (ii) acetate, (iii) lactate and (iv) gluconate and (v) mixtures thereof.

Chloride is generally the preferred anion. Said dry first granular product is admixed with finely divided (ca. −60 to +200 mesh) anhydrous sodium bicarbonate to form a composition which is representative of the first sodium bicarbonate system of this invention.

As with the sodium acetate system, radio frequency (microwave or electromagnetic) heating is preferred when preparing granular products of the first sodium bicarbonate system, but other heating methods (including those using conduction and convection) are operable.

The granular products of the first sodium bicarbonate system are similar to the granular products of the above-discussed sodium acetate system except that: (a) sodium bicarbonate is the sole or principal (major) alkalyzing agent in the first sodium bicarbonate system while sodium acetate is the sole or principal alkalyzing agent in the granular products of the sodium acetate systems and (b) dry sodium bicarbonate is admixed with dry, chemically homogeneous granules of the other components to form the first sodium bicarbonate system.

Likewise, dialysis solutions (i.e., solutions for use in hemodialysis or peritoneal dialysis) prepared from the granular products of the first sodium bicarbonate system are the same as those prepared from the sodium acetate solutions except that sodium bicarbonate is the sole or principal alkalyzing agent in solutions prepared from the granular products of the first sodium bicarbonate system while sodium acetate is the sole or principal alkalyzing agent in compositions of the sodium acetate system.

Second Sodium Bicarbonate System

The second sodium bicarbonate system is an admixture of dry, free-flowing, non-caking particulate: (a) sodium chloride (b) a physiologically acceptable ionic salt of magnesium; (c) a physiologically acceptable ionic salt of calcium; (d) sodium bicarbonate; and (e) a minor amount of sodium acetate if required. Said magnesium and calcium salts may have ions selected from the group consisting of: (i) chloride; (ii) lactate; (iii) gluconate and (iv) acetate. Lactate, acetate and gluconate ions, if present, are present in minor amounts. Minor amount of potassium ions may also be present.

The second sodium bicarbonate system is prepared by drying the individual salts which will comprise the system and mixing them after drying and sizing (classifying, e.g., screening). Radio frequency (microwave) heating is preferred for drying materials when preparing granular products of the second sodium bicarbonate systems but other heating methods are operable.

If required by the patient, materials such as the potassium chloride can be included in the second sodium bicarbonate system. If desired, when including potassium, at least a portion of the potassium may be added as potassium bicarbonate.

Also, if required by the patient, anhydrous dextrose may be incorporated into dry compositions of the first or second sodium bicarbonate systems. Alternatively, the dextrose can be added to the water in which such bicarbonate system is dissolved to form a hemodialysis solution or a peritoneal dialysis solution.

Currently used dialysis procedures do not ordinarily take into account those materials in blood that are protein bound. Examples are iron, zinc, copper and cobalt. Traditionally, these materials are administered as separate medicants. However, it is an object of this invention to make such materials an integral part of dry dialysate products. Physiologically acceptable amounts of finely divided physiologically acceptable soluble salts containing materials which are normally protein bound in blood can be included in products of this invention. Thus, therapeutic requirements of such materials may be supplied during the dialysis procedure.

The granular products of this invention are, as noted supra, useful for preparing hemodialysis solutions and peritoneal dialysis solutions.

The following disclosure will make the above and other objects of this invention readily apparent to those skilled in the art.

DESCRIPTION OF THE PREFERRED EMBODIMENTS

Figure 1:
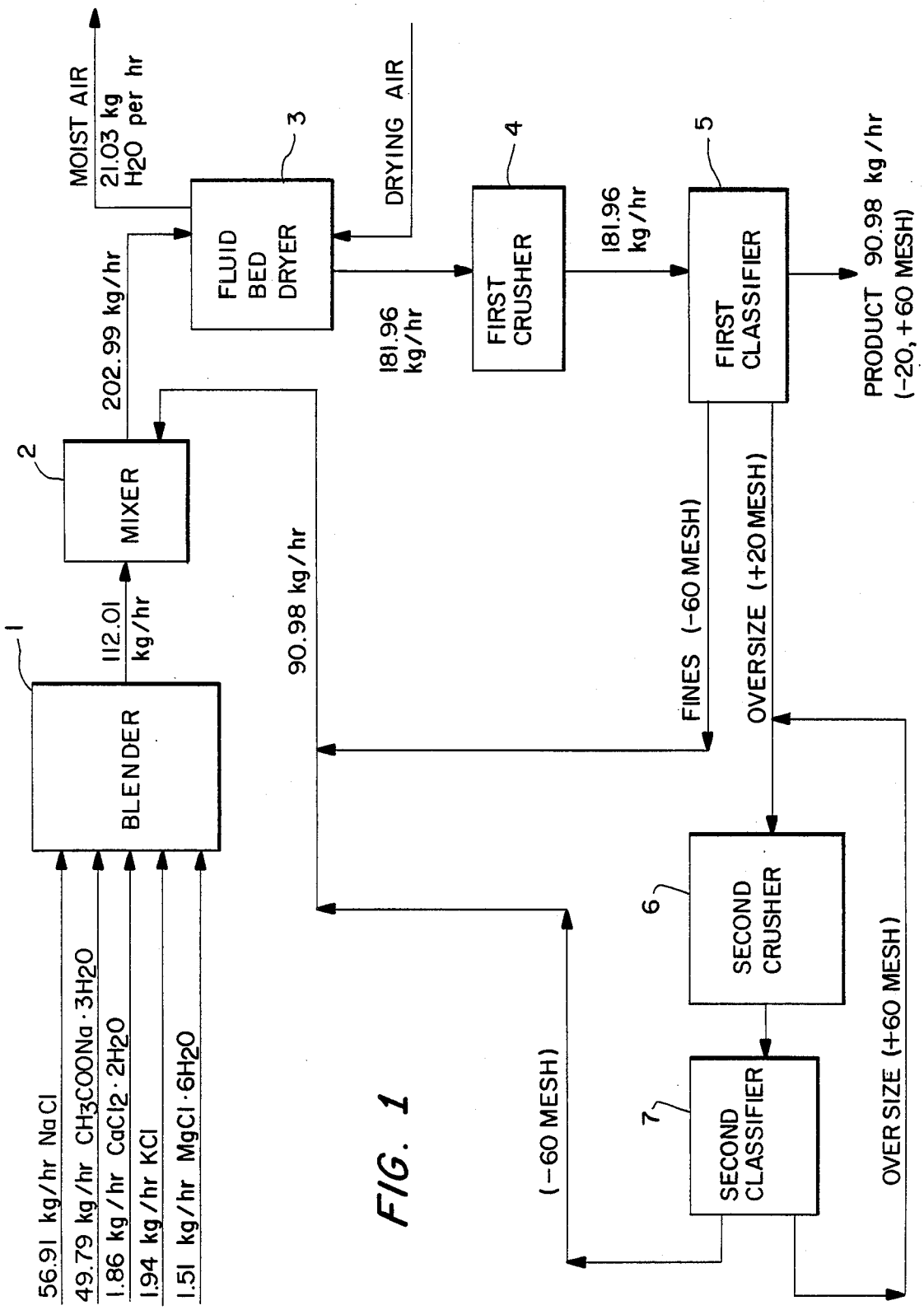
FIG. 1 is a flow-sheet of the embodiments of this invention exemplified by Examples 4 and 11.

As noted supra, hemodialysis solutions are used in the process known as "hemodialysis", which is also referred to as "dialysis", to remove waste products of metabolism from the blood of a patient having renal deficiency. This is done by contacting the blood through a semi-permeable membrane with a suitable dialysis solution such that the waste products in the blood are removed from the blood and pass into the dialysis solution. It is essential that the dialysis solution contain various ions in specific concentration so that these will not be extracted from the patient's blood.

In peritoneal dialysis (which is also known as dialysis), a dialysis solution is injected into a patient's abdominal cavity where waste products are filtered from the patient's blood, through his peritoneal membrane into the dialysis solution which, after taking up the waste products, is withdrawn from the abdominal cavity and discarded.

Human blood contains trace quantities of many materials, but the most important components of concern in hemodialysis and in peritoneal dialysis solutions are sodium, potassium, calcium, magnesium, chlorine, hydrogen and hydroxyl ions and dextrose. The composition of blood varies from individual to individual. This necessitates using dialysis solutions having specific characteristics to satisfy the needs of each patient. Fortunately, a few formulations are effective to cover most patients—requiring only minor on-site use of modification to meet the needs of the patient. The following formulations, based on the use of sodium acetate as alkalyzing agent, are typical of aqueous solutions which are adapted for use in hemodialysis and peritoneal dialysis:

| Formulation | mEq per liter[1] | | | | | Sodium Acetate |
|---|---|---|---|---|---|---|
| | Na[2] | K | Ca | Mg | Cl | |
| A | 134 | 2.5 | 2.5 | 1.5 | 104 | 36.5 |
| B | 134 | — | 2.5 | 1.5 | 101.4 | 36.6 |
| C | 130 | 2.0 | 2.5 | 1.5 | 100. | 36.0 |
| D | 132 | 1.5 | 3.25 | 1.25 | 101 | 37.0 |
| E | 132 | 1.5 | 3.25 | 1.25 | 101 | 37.0 |
| F | 134 | — | 2.5 | 1.5 | 101.4 | 36.6 |

-continued

| Formulation | Na[2] | mEq per liter[1] | | | | Sodium Acetate |
| --- | --- | --- | --- | --- | --- | --- |
| | | K | Ca | Mg | Cl | |
| G | 132 | — | 3.25 | 1.25 | 100 | 36.5 |

[1]Note the relative constancy of Na, Mg, Cl and acetate. K and Ca are main variants. In special cases, when specified by the physician, calcium chloride and/or magnesium chloride can be omitted. Sodium bicarbonate may replace sodium acetate. Dextrose may be added to these formulations if required.
[2]Total sodium.

Solutions for use in hemodialysis and/or peritoneal dialysis can be prepared by dissolving the granular product of this invention in sterile purified water. Since dextrose (glucose) is frequently a component of such solutions, the granular product of this invention can be mixed with anhydrous dextrose to prepare a dry particulate composition which will dissolve in said water to form a dextrose-containing solution adapted for use in hemodialysis and/or peritoneal dialysis. The amount of dextrose required can vary from patient to patient. Hence, different compositions containing different ratios of dextrose to said granular product can be prepared providing that the ratios are such that the compositions, when dissolved in sterile purified water, will produce solutions operable in hemodialysis or peritoneal dialysis. However, it should be noted that dextrose need not be admixed with said granular product because (a) some patients may not require dextrose, and (b) dextrose, if required, can be added while preparing a solution from the granular product of this invention for use in hemodialysis or peritoneal dialysis. Alternatively, the dextrose can be added to such solution prepared from the granules of this invention or to sterile purified water which will be used in preparing such solution.

In one embodiment, where using sodium acetate as alkalyzing agent, the instant invention is directed to a process for preparing a dry granular product which, on solution in water, is capable of producing a hemodialysis or peritoneal dialysis solution.

In another embodiment, where using sodium bicarbonate as the alkalyzing agent, this invention is directed to a process for preparing a dry granular product comprising dry granular sodium bicarbonate, which can be dissolved in water to produce a hemodialysis or peritoneal solution.

Granular product of the first sodium bicarbonate system is preferably prepared by the rapid vaporization of water from an aqueous mixture wherein the water is provided: (a) in the form of water of hydration of at least one of the components (salts) to be granulated (i.e., incorporated into the product granules); (b) as liquid water in an amount sufficient to dissolve all of said salts present in the aqueous mixture, wherein the aqueous mixture is a solution; or (c) as liquid water in an amount insufficient to dissolve all of said salts present in the aqueous mixture wherein the aqueous mixture is a dispersion of small (minute) particles of at least one of said salts in a solution of said salts. Said small particles produce no feeling of graininess when rubbed between one's fingers and generally pass a 200-mesh U.S. standard screen.

Under the conditions used to prepare the intimately admixed granular products of this invention, it is physically impossible to grow large, well-ordered crystals visible to the naked eye. As observed under the microscope, the intimately admixed granular products of this invention consist of an interlocked mass of small individual species (crystals or amorphous particles) unrecognizable to the naked eye. The particles have no specular characteristics (as would evidence a light-reflecting crystal plane of visual magnitude). When broken, the granules have a lusterless conchoidal fracture, which further confirms the existance of very small individual material domains rather than large crystals. The fact that the granules of this invention have a microporous structure is evidenced further by the rapid manner in which the unique particles of this invention dissolve when contacted with water.

While any type of indirect heating can be used to remove water from an aqueous system to obtain a granular product of this invention, electromagnetic energy (e.g., ratio frequency (RF) or microwave (MW) energy) is particularly effective for accomplishing the rapid vaporization of water which is important to obtain the highest quality product.

The use of electromagnetic energy to produce heat for vaporizing water while operating under reduced pressure to facilitate the removal of water as water vapor is particularly advantageous when preparing the compositions of this invention.

It has been found that solubility properties, especially rate of solution, of two or more ionic salts comprising a solid mixture is greatly influenced by the nature of the individual salt particles and the association of such particles with each other prior to the instant of contact with water. Simple physical mixtures of individual particles of at least two hydrated and/or anhydrous salts dissolve markedly more slowly to form a desired homogeneous solution than does a composite granular material of comparable particle size and the same overall chemical composition, wherein each granule comprises an intimate association of very small particles of each of the several individual components or materials comprising the individual granules. A composition comprising such an intimate association or admixture of several very small indivdual particles of components can be prepared by first homogeneously mixing hydrated, or partially hydrated, salts or melts or solutions thereof, and subsequently removing the water rapidly to cause simultaneous deposition en masse of mixed small particles, each small particle being: (a) invisible to the naked eye; and (b) anhydrous or partially hydrated. Finely divided salts, not capable of forming hydrates may be included in the hydrous composition prior to the rapid removal of water. Each product granule which is visible to the naked eye is an intimate interlocked admixture of very small particles of each constituent.

As set forth in more detail elsewhere in this specification, the composition of the first sodium bicarbonate system of this invention is prepared by preparing granules which do not contain sodium bicarbonate and admixing finely divided (e.g., −60 +200 mesh, U.S. standard) sodium bicarbonate and the dry sodium bicarbonate-free granules.

The foregoing discovery has been found particularly useful for the preparation of dry concentrates comprising compositions of the sodium acetate system or the first sodium bicarbonate system of this invention which are useful in hemodialysis and peritoneal dialysis.

The term "dry" in this specification means that there is no water present that is capable of participating in, or facilitating reaction between, constituents. As applied to the compotions of the first sodium bicarbonate system and the sodium acetate system of this invention, said term means a material lacking the quality of wetness and which, in a granular form, is free-flowing and non-caking. Dry products of this invention may contain individual constituents having trace amounts of bound water of hydration.

In hemodialysis and peritoneal dialysis, it is very important that the composition of salt concentrates and their solubility characteristics be precisely and reliably controlled. Such control is readily obtained using the products of this invention, especially the compositions of the sodium acetate system and the first sodium bicarbonate system.

In hemodialysis and peritoneal dialysis, it is very important that materials from which the dialysis solution is prepared be sterile. Accordingly, the granules of this invention are preferably prepared and packaged under sterile conditions, thereby avoiding a subsequent sterilization step. Sterility to the user is assured by adequate protective packaging.

Although I do not wish to be bound by theory, I believe the granules of the sodium acetate system and the first sodium carbonate system of this invention may owe their rapid solubility properties, at least in part, to the fact that various salt hydrates do not lose their water of hydration at the same rate in a given environment. Because of this fact, when a complex mixture comprising a solution of an intimate (or so-called "chemically homogeneous") mixture of hydrated or partially hydrated salts or melts or solutions thereof is dried rapidly (partially or totally), there is little time for any one pure crystal to grow in an orderly manner. Rather, in each granule, a myriad of small intermixed crystals or amorphous particles of the individual materials present is obtained. Further, the granules have a degree or porosity caused by the sequential departure of water from the interstatial spaces left between the several components comprising the granules. The rapid solubility characteristics of products of this invention, in large part, may be due to the disordered, small individual component particles and the microporous nature of the materials comprising the granules. Some partially hydrated species may be included in each granule and, by their presence, may increase the rate of solution when the granule is dissolved.

Conventional crystallization procedures are not applicable to the production of the granular products of the sodium acetate and first sodium carbonate systems of this invention. The art of crystallization has been developed extensively over the years. Much effort has been directed towards obtaining pure compounds from solutions of mixed materials. When a solution is supersaturated with respect to a specific salt, that salt tends to crystallize out as a pure solid phase if a suitable seed material is present. The formation of large, well-formed crystals of a pure material requires that the crystallization procedure be conducted slowly, allowing time for well-ordered pure crystals to grow. If one shocks the system, as by rapid temperature change or physical agitation, large pure crystals are not obtained. On the contrary, a mixture of disoriented smaller crystals results, tending to defeat the generally desired objective of conventional crystallization operations.

This invention is directed to an improved means of preparing a multi-component stable, dust-free, readily soluble granular product for dialysis solution preparation. Because of fractionation, conventional crystallization processing is not an operable method for making the product of this invention.

The sodium bicarbonate systems of this invention are dry, readily soluble, stable, free-flowing compositions which when dissolved in water produce relatively stable bicarbonate dialysis (hemodialysis and peritoneal dialysis) solutions of the type illustrated by the above-mentioned Bulletin of Renal Systems, Inc.

As mentioned supra, dextrose is not required by all patients. In the processes and compositions of the instant invention, including all sodium acetate and sodium bicarbonate systems, it (dextrose) is treated as an optional component and handled as a separate entity.

Dextrose may be added as an anhydrous material and be a part of the granular product (based on sodium acetate or on sodium bicarbonate) of this invention, or it may be added as a solution to dialysate solutions made from granular products of this invention. However, dextrose is never combined with the other components of the compositions of this invention prior to the water removing step wherein said other components are rendered dry.

Further, to avoid reaction between bicarbonate and calcium and magnesium salts during the preparation of dialysate solutions based on sodium bicarbonate, the sodium bicarbonate is, as set forth above, treated as a separate entity and admixed with the other solid components after the removal of water from said solid components because, in the absence of water in which said solid components (and sodium bicarbonate) can dissolve, calcium and magnesium salts do not react with the sodium bicarbonate to form insoluble carbonates.

In the preparation of the compositions of the above-mentioned first sodium bicarbonate system, I found that if solutions of the calcium and magnesium salts and sodium acetate required are first co-mingled with finely divided sodium chloride, followed by rapid evaporation of water as taught by parent application Ser. No. 123,355 filed Feb. 21, 1980 and now abandoned a dry solid comprising an intimate mixture of micro-particles of the individual salts is obtained. Further, I found that this substantially anhydrous composition comprising calcium and magnesium chlorides (and optionally, minor amounts of sodium acetate) in finely divided intimate admixture with micro-crystalline sodium chloride, can be admixed with finely divided anhydrous sodium bicarbonate and, optionally, finely divided anhydrous dextrose to form the first sodium bicarbonate system of this invention which is stable in the dry state and which dissolves readily in physiologically acceptable water to form a diluted solution suitable for dialysis use. It was also found that compositions of said first sodium bicarbonate system (with or without dextrose) can be dissolved in water (having a pH adjusted to about 6.5), using a small amount of acetic acid—for example, a few ml of a 5% solution of acetic acid per liter of water used to form stock stable solutions having constituent concentrations two to three times that required for dialysis use.

It was also found that a less preferred composition of this invention (the above-described second sodium bicarbonate system) can be made by simply mixing finely divided substantially anhydrous calcium chloride, magnesium chloride and sodium chloride with finely divided dry sodium bicarbonate. It was found that such mixtures can be dissolved in water to form solutions suitable for dialysis use, but that concentrates of, for instance, twice or three times use concentration are relatively unstable—as evidenced by the early onset of precipitation of calcium and magnesium carbonates.

Bicarbonate comprising dialysate solutions made from compositions of the aforesaid first sodium bicarbonate system of this invention are remarkably more stable than similar solutions prepared by adding solid sodium bicarbonate (or a concentrate sodium bicarbonate solution) to a solution comprising the other components according to the teachings of the prior art in that dialysis solutions prepared from compositions of said first sodium bicarbonate system have substantially no tendency to precipitate calcium carbonate and/or magnesium carbonate.

Preferred solid granular solids of the first sodium bicarbonate systems of this invention having the same ratios of sodium ions, calcium ions, bicarbonate ions and acetate ions as the above described Solution A can also be used to prepare "double use strength" stock solutions having double the concentration of said solution A which are stable for over 72 hours without any indication of calcium carbonate or magnesium carbonate precipitation when maintained at a pH of 7.2 to 7.4. After standing for 96 hours, a small but visible amount of precipitate was observed in such double strength (double use concentration) stock solutions prepared from the first sodium bicarbonate system of this invention. Such double strength stock solutions can be diluted with an equal weight of water to prepare solutions useful as hemodialysis and as peritoneal dialysis solutions.

Attempts to prepare such double strength solutions using simple dry mixture formulations of the second sodium bicarbonate system resulted in the almost instantaneous precipitation of calcium carbonate and magnesium carbonate.

Such lesser stability of simple mixture formulations may be caused by localized high concentrations which result when solid sodium bicarbonate (or a concentrated sodium bicarbonate solution) is admixed with and dissolved in a solution containing magnesium chloride and calcium chloride. There is substantially no chance of obtaining such a localized high concentration when using the first sodium bicarbonate system of this invention.

The anions and cations (excluding dextrose, which is not ionic) present in one liter of undiluted commercially available dialysis solution, such as Solution A, are:

| | |
|---|---|
| $Na^+$ | 3.2196 grams |
| $Ca^{++}$ | 0.0701 grams |
| $Mg^{++}$ | 0.0182 grams |
| $Cl^-$ | 3.7577 grams |
| Bicarbonate Ions | 2.1350 grams |
| Acetate Ions | 0.2362 grams |
| | 9.4368 grams total |

As taught by the instant invention, these ions in the concentration required for one liter of dialysis solution can be supplied by:

| | |
|---|---|
| NaCl | 5.9034 grams |
| $CH_3COONa$ | 0.3280 grams |
| $CaCl_2$ | 0.1941 grams |
| $MgCl_2$ | 0.0713 grams |
| $NaHCO_3$ | 2.9400 grams |
| | 9.4368 grams total |

The following examples illustrate embodiments whereby the product of this invention can be prepared. Said invention will be better understood by referring to said examples which are specific but non-limiting. It is understood that said invention is not limited by these examples, which are offered merely as illustrations. It is also understood that modifications can be made without departing from the spirit or scope of the invention.

Examples 1–6 illustrate the preparation of compositions of the sodium acetate system of this invention. Examples 7–14 illustrate the preparation of compositions of the first sodium bicarbonate system of this invention, while Example 15 illustrates the preparation of a composition of the second sodium bicarbonate system of said invention.

Figure 2:
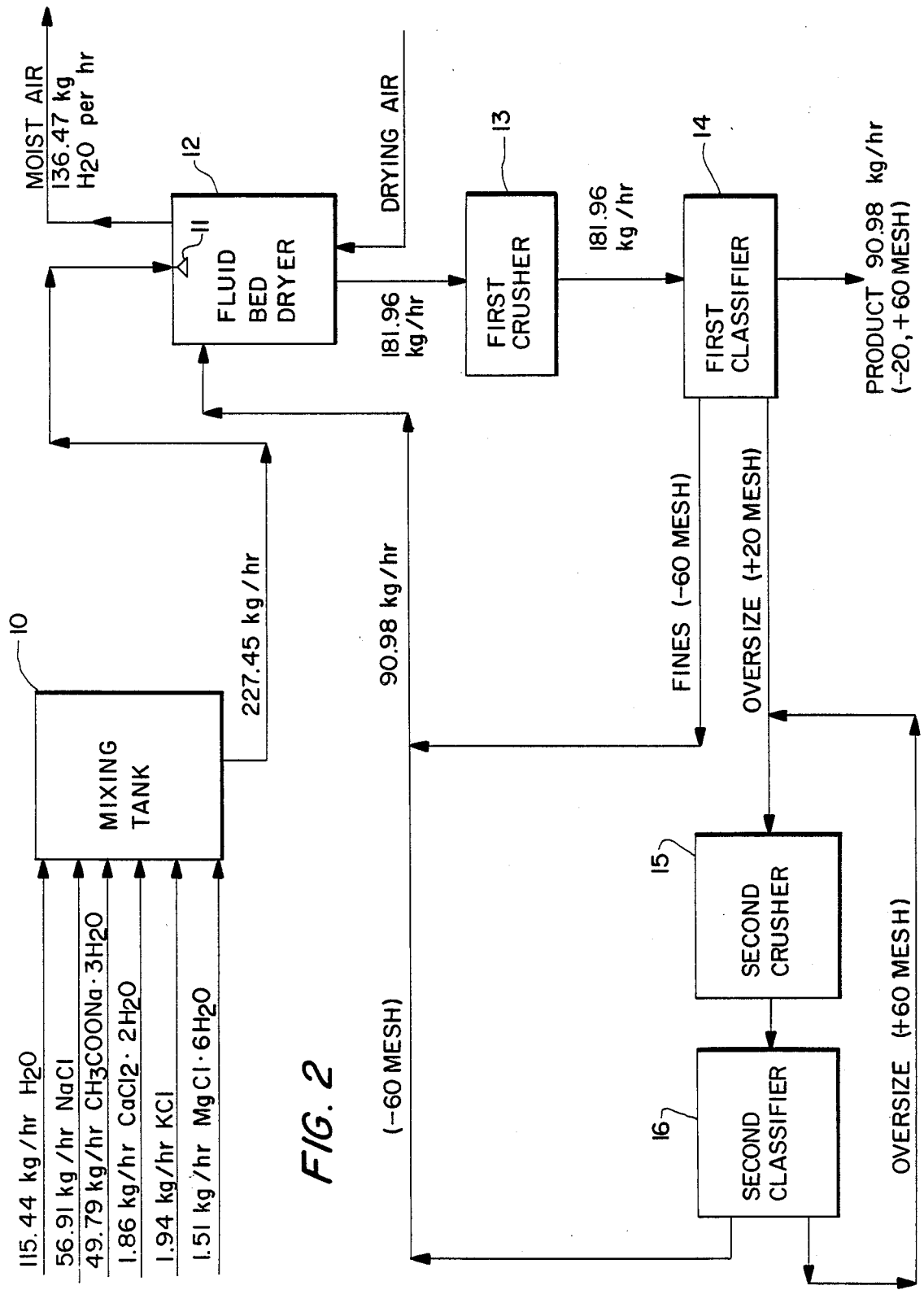
FIG. 2 is a flow-sheet of the embodiments of this invention exemplified by Examples 5 and 12.
Figure 3:
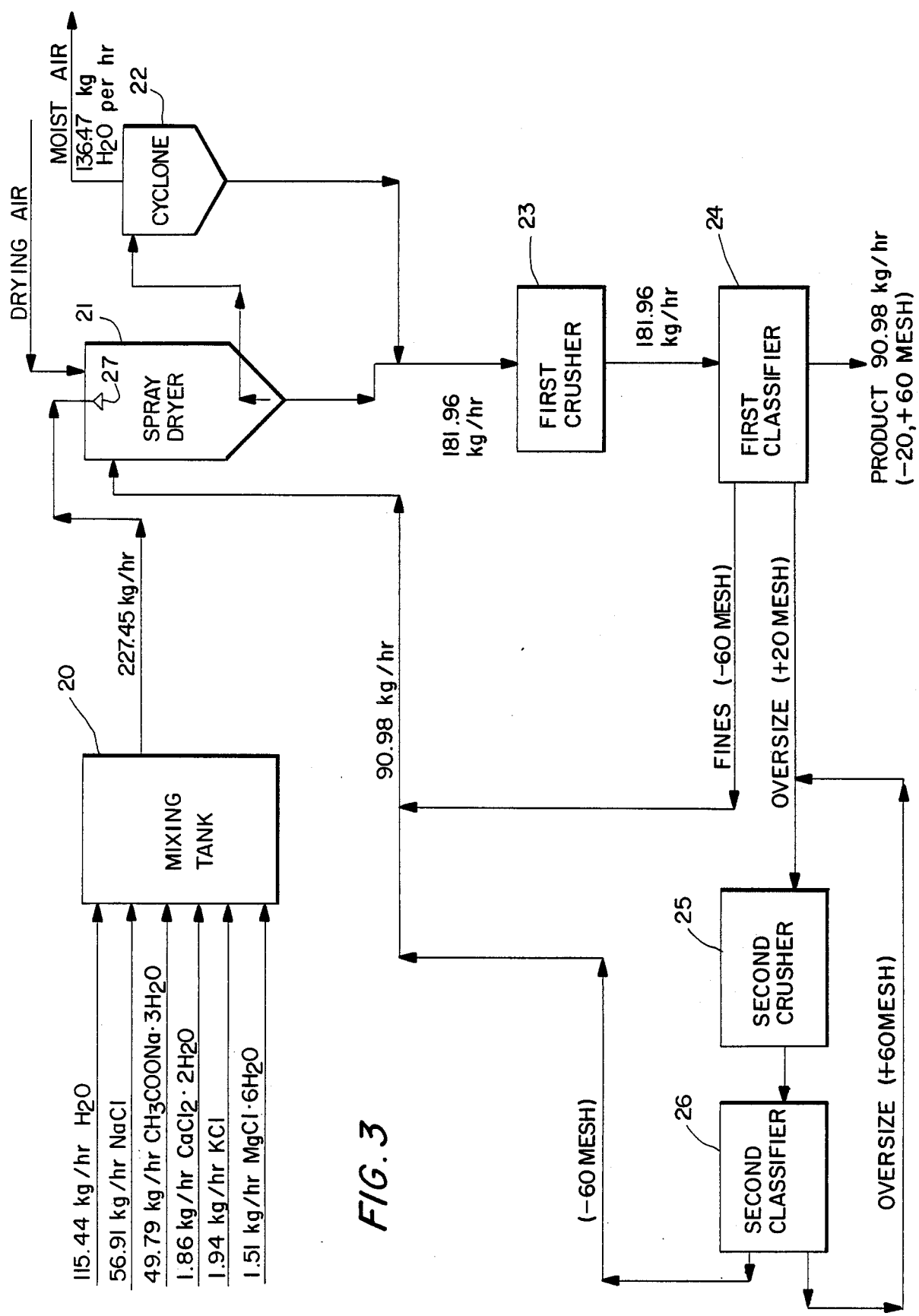
FIG. 3 is a flow-sheet of the embodiments of this invention exemplified in Examples 6 and 13.

Referring to FIGS. 1, 2 and 3, it should be noted that if preparing a composition which does not contain potassium chloride, the feed line labelled "KCl" can be disconnected or the feeding of potassium chloride can be simply omitted. Likewise, if a composition which does not contain sodium acetate is being prepared, the line labelled "$CH_3COONa$" can be disconnected or the feeding of sodium acetate can be omitted. The $H_2O$ line is closed (no water is fed into blender 1) in the run described in Example 4, but water is fed into said blender in the run described in Example 11. If it is desired to feed another component, such as sodium lactate or sodium gluconate, an additional line can be provided. Likewise, two additional feed lines (not shown) can be provided if two additional components, e.g., sodium lactate and potassium gluconate, are to be included in the granular product (or intermediate product) exit the first classifier. Water can be added when required and hydrates of compounds such as sodium acetate, magnesium chloride and calcium chloride, which forms hydrates, can be used when required or desired. The use of hydrates can reduce the amount of water required.

Examples 1–6 illustrate the preparation of compositions of the sodium acetate system

EXAMPLE 1

(Thin Section Drying)

$CH_3COONa.3H_2O$ (174.1 g), $CaCl_2.2H_2O$ (6.5 g), $MgCl_2.6H_2O$ (5.3 g), NaCl (199 g) and KCl (6.8 g) were intimately mixed by handworking in a mortar to produce a chemically homogeneous mixture which was non-gritty to the feel and felt paste-like (semi-fluid). The mass (391.7 grams) had a calculated water content of 18.8%. Rapid drying in thin section (less than 7 mm thick) in a vacuum oven set at 120° C. under static conditions produced a granular product weighing 318 grams. This was near the theoretical anhydrous weight. Said product was crushed and passed through a 20-mesh U.S. standard screen. The resulting product granules which passed through said screen were dust-free and readily and completely dissolved in water at 30.5° C. with gentle stirring in less than three minutes to form a 30% solids by weight solution.

A simple mixture of comparable commercial materials required more than ten minutes to obtain the desired 30% solution

EXAMPLE 2

(Thin Section Drying)

$(CH_3COO)_2Mg.4H_2O$ (12.9 g), KCl (17.9 g), $CaCl_2.2H_2O$ (26.5 g), $CH_3COONa.3H_2O$ (555.5 g) and NaCl (673.2 g) were ground together in a mortar at about 60° C. to form a pasty mass. This pasty mass was tray dried in thin section (less than 1.6 mm thick) in an oven at 120° C. The resulting dried product weight was 1,070 grams (which was near the theoretical dried weight). Said product was crushed in a mortar and passed through a 20-mesh screen. The product granules passing through the 20-mesh screen were free-flowing and dust-free. They readily and completely dissolved in water at 30.5° C. with gentle stirring in less than three minutes to form a 30% (dissolved solids content) solution.

A simple mixture of comparable commercial materials required more than ten minutes to obtain a similar (30%) solution

EXAMPLE 3

(Thin Section Drying)

$(CH_3COO)_2Mg.4H_2O$ (12.9 g), KCl (17.9 g), $CaCl_2.2H_2O$ (26.5 g), $CH_3COONa.3H_2O$ (555.5 g) and NaCl (673.2 g) were ground together in a mortar at about 60° C. to form a pasty mass designated "Composition 1". A 120.7 gram portion of Composition 1 was spread in thin section (ca. 7 mm thick) on a glass tray and placed in a Thermidor microwave oven made by Norris Industries of Los Angeles, Calif., at a "low heat" setting. Drying to constant weight was accomplished in approximately six minutes. It was noted that 21.5 grams of water was evaporated. This compares closely to the 20.7 grams of water of hydration associated with the sodium acetate and the other hydrates contained in the sample. The sample temperatures could not be measured during the heating process, but the glass tray was only warm to the touch on removal from the oven, indicating that dehydration was accomplished at a relatively low temperature.

The product from this experiment was pulverized and passed through a 20-mesh screen. The material was chemically homogeneous, dust-free and free-flowing. It readily and completely dissolved in less than three minutes in water at 30.5° C. with gentle stirring to form a 30% solids content solution.

In a separate run, using another portion of Composition 1 and the "high heat" setting of the microwave oven, rapid charring of the sodium acetate was observed.

This example clearly shows that electromagnetic energy (e.g., radio frequency or microwave energy) can be used to rapidly remove water from complex salt mixtures to form dry, free-flowing, stable, dust-free particulate (granular) chemically homogeneous products of this invention.

In a commercial process employing electromagnetic energy, finely divided recycled particles can be employed. A gas stream can be used to help rapidly remove water vapor from the system. Such electromagnetic energy dehydration process can be conducted in a thin section stationary manner, in a fluid bed or in an ebullient bed. Vacuum or reduced pressure may be employed to aid in rapid water removal.

EXAMPLE 4

(Fluid Bed Drying with Recycle)

The dry, free-flowing, stable, non-caking, dust-free chemically homogeneous granular product of this invention can be prepared in a continuous manner by using the following procedure, which is designed to produce, per hour of plant operation, granular product sufficient for 100 unit hemodialysis treatments.

Referring to FIG. 1: NaCl (56.91 kg), $CH_3COONa.3H_2O$ (49.79 kg), $CaCl_2.2H_2O$ (1.86 kg), KCl (1.94 kg) and $MgCl_2.6H_2O$ (1.51 kg) are co-mingled in blender 1 to form a fluid pasty mass at a rate of 112.01 kg/hr. Said fluid pasty mass (112.01 kg/hr) is passed (e.g., by a conveyor belt, screw conveyor or the like) proportionally and in a continuous manner, and at a rate of 112.01 kg/hr, to first mixer 2 where it is intimately admixed with 90.98 kg/hr of ground or crushed oversize and fine recycle material from a later-recited sizing (crushing and classifying) operation to form a granular particulate mass which is passed at the rate of 202.99 kg/hr to the fluid bed dryer 3 where it is contacted with drying air having a flow rate and temperature effective for maintaining the temperature within the bed dryer 3 at 130° C. Water is vaporized from the fluid bed at the rate of 21.03 kg/hr. Dry product from fluid bed dryer 3 is passed at the rate of 181.96 kg/hr to first crusher 4 where it is crushed. Crushed product (181.96 kg/hr) is passed from the first crusher 4 to the first classifier 5 from which 90.98 kg/hr of granular particles passing through a 20-mesh screen and retained on a 60-mesh screen are collected as product, and the particles (90.98 kg/hr) retained on a 20-mesh screen or passing a 60-mesh screen are recycled. Particles passing the 60-mesh screen are recycled directly to first mixer 2 while those retained on the 20-mesh screen are passed to second crusher 6 and from there to second classifier 7. Oversize particles (particles retained on a 60-mesh screen) are recycled from second classifier 7 to second crusher 6 while those passing through said 60-mesh screen are passed to first mixer 2 as recycle.

EXAMPLE 5

(Fluid Bed Drying with Recycle)

The dry, free-flowing, stable, non-caking, chemically homogeneous dust-free granular product of this invention can also be prepared in a continuous manner by using the following procedure, which is designed to produce product for 100 unit hemodialysis treatments per hour of plant operation.

Referring to FIG. 2: NaCl (56.91 kg), $CH_3COONa.3H_2O$ (49.79 kg), $CaCl_2.2H_2O$ (1.86 kg), KCl (1.94 kg), $MgCl_2.6H_2O$ (1.51 kg) and water (115.44 kg) are mixed in first mixer 10 to form, at a rate of 227.45 kg/hr, a concentrate (solution) having a 40% dissolved solids content. The resulting solution is preheated under pressure to about 130° C. (using any conventional indirect heating means, not shown) and introduced as a fine spray from nozzle 11 (e.g., a spray head nozzle such as a hollow-cone nozzle, a solid-cone nozzle, a fan nozzle, an impact nozzle, a rotating disc nozzle or the like), into a fluid bed dryer 12 (where said solution is contacted with an air stream having a temperature and flow rate effective for maintaining a bed temperature of about 130° C). Fluid bed dryer 12 contains a bed of previously prepared granules having a composition substantially the same as that obtained by vaporizing the water from said concentrate and having diameters of up to about 6.5 mm. The introduced solution is distributed over the surfaces of the granules within fluid bed dryer 12 which, as noted supra, has an internal temperature of about 130° C. The granules in the fluid bed dryer comprise a mixture of recycled product from a later recited sizing (crushing and classifying) step and resident granular material held in the bed for contact time purposes. Water is evaporated from the solution added to the fluid bed dryer at the rate of 136.47 kg/hr to yield 181.96 kg/hr of dried effluent. Said dried effluent is passed from fluid bed dryer 12 to first crusher 13 and from said first crusher to first classifier 14 at a rate of 181.96 kg/hr. Granular product passing a 20-mesh screen and retained on a 60-mesh screen is collected at the rate of 90.98 kg/hr while fines (particles passing a 60-mesh screen) and oversize particles (particles retained on a 20-mesh screen) totalling 90.98 kg/hr are used as recycle. The fines are passed from first classifier 14 to fluid bed dryer 12, while oversize material is passed from first classifier 14 to second crusher 15. The oversize material, after being crushed in second crusher 15, passes to second classifier 16 where it is classified. Oversize material from second classifier 16 (i.e., particles retained on a 60-mesh screen) are recycled to second crusher 15 while material passing through a 60-mesh screen is recycled to fluid bed dryer 12.

EXAMPLE 6
(Spray Drying with Recycle)

The dry, free-flowing, stable, non-caking, dust-free chemically homogeneous granular product of this invention can be prepared in a continuous manner by using the following procedure, which is designed to produce sufficient product for 100 hemodialysis treatments per hour of plant operation.

Referring to FIG. 3: NaCl (56.91 kg), $CH_3COONa.3H_2O$ (49.79 kg), $CaCl_2.2H_2O$ (1.86 kg), KCl (1.94 kg), $MgCl_2.6H_2O$ (1.51 kg) and water (115.44 kg) are mixed in first mixer 20 to prepare a concentrated feed solution designated "Solution A-6" containing 40% dissolved solids in the amount of 227.45 kg/hour. This concentrated solution is pre-heated under pressure to about 150° C. (using any conventional indirect heating means, not shown) and passed into spray dryer 21 in the form of small droplets from nozzle 27 (which can be a nozzle of the type described in Example 5, supra) where droplets are contacted with (a) a stream of heated drying air having a temperature and flow rate effective for forming the dry, granular product of this invention, and (b) a stream of 90.98 kg/hour of finely divided (−60 mesh) recycled product material from a later recited sizing (crushing and classifying step).

Air exits from spray dryer 21 carrying with it 136.47 kg/hr of water and then passes through cyclone 22 before being vented to the atmosphere.

Dried product (181.96 kg/hr) exits from the lower section of spray dryer 21 in two portions, a first portion and a second portion. Said first portion passes directly from said spray dryer 21 to first crusher 23, while said second portion passes (with air exit spray dryer 21) to cyclone 22 where said second portion of dried product is collected and passed to first crusher 23. Crushed product from first crusher 23 passes to first classifier 24 at a rate of 181.96 kg/hr. Granular product from first crusher 23 passing a 20-mesh screen and retained on a 60-mesh screen is collected as product at the rate of 90.98 kg/hr while fines (particles passing a 60-mesh screen) and oversize particles (particles retained on a 20-mesh screen) totalling 90.98 kg/hr are used as recycle. The fines are passed from first classifier 24 to spray dryer 21, while oversize material is passed from first classifier 24 to second crusher 25. The oversize material, after being crushed in second crusher 25, passes to second classifier 26 where it is classified. Oversize material from second classifier 26 (i.e., particles retained on a 60-mesh screen) are recycled to second crusher 25 while material passing through the 60-mesh screen is recycled to spray dryer 21.

A granular, substantially dry product, made by simulating the process of this Example (Example 6) was dust-free and dissolved readily and completely in less than three minutes in 30.5° C. water to form a 30% solids content concentrated solution.

Said process was simulated by placing a small amount of a solution having the same composition as the above-mentioned Solution A-6 along with a calculated amount of dry simulated recycle material having the same composition as the solids of Solution A-6, mixing them together with a spatula to form an admixture, placing the admixture on an electrically heated surface, and rapidly drying said admixture with a stream of warm air from a "hot air blower".

Examples 7–14 illustrate the preparation of compositions of the first sodium bicarbonate system

EXAMPLE 7
(Thin Section Drying)

The materials used in this Example were Reagent Grades of anhydrous calcium chloride, magnesium chloride, sodium acetate, sodium bicarbonate, and U.S.P. sodium chloride. All materials were dried to constant weight in a Thermador microwave oven made by Norris Industries of Los Angeles, Calif. No loss in weight was noted using the "low heat" setting. Thus, said starting materials used in this Example were deemed anhydrous, as evidenced by no weight loss when subjected to electromagnetic energy, used as a source of heat for obtaining dry products in this and the following Examples.

$CaCl_2$ (1.941 grams) and $MgCl_2$ (0.713 grams) were placed in a 9" diameter pyrex pie plate to which was added 15 grams of water. The water totally dissolved the calcium and magnesium chlorides. NaCl (59.034 grams) was added to the solution in the dish. A gentle rubbing action with a spatula was sufficient to form a fluid mass indicating that the magnesium and calcium chloride salts were thoroughly intermixed with the dissolved sodium chloride and a few remaining small solid particles of sodium chloride. Sodium acetate (3.28 grams) was then added and the mixing action continued to assure thorough intermixing of said materials in the aqueous medium. The fluid, semi-pasty mass was then spread uniformly in the pie plate and subjected to electromagnetic heating to rapidly remove the water present. Approximately 10 grams of water was evaporated in the first two minutes of heating.

After an additional two minutes of heating, it was found that the 15 grams of water added had been evaporated and a mixed micro-particulate product formed. An additional two minutes of heating produced no further weight loss, indicating that the product was anhydrous as defined in this specification. The 4.96 grams of material from the foregoing procedure was ground in a mortar to pass a 20-mesh screen and admixed with −60+200 anhydrous $NaHCO_3$ (29.4 grams), to form 94.36 grams of the abovementioned first sodium bicarbonate system of this invention.

On a per liter of diluted-for-use basis, 9.4368 grams of the product of this Example, Example 7 (when dissolved and diluted to 1 liter) provides the ion concentrations commercially used as represented by Renal Systems SB-600.

For laboratory check purposes (i.e., a simulated use run), to observe the diluted product stability of the product of this Example (Example 7) against the precipitation of $CaCO_3$ and $MgCO_3$, 1.887 grams (9.4368 divided by 5) of said product was added to 200 ml of deionized water (1000 divided by 5) having a pH of 6.5. A clear solution having a pH of 7.8, as measured on a precision pH meter calibrated against standardized buffer solutions, was obtained. The solution remained clear for 72 hours, indicating little tendency for $CaCO_3$ or $MgCO_3$ precipitation. After about 96 hours, a small but visual amount of precipitate was noted, indicating precipitation of some calcium carbonate and/or magnesium carbonate.

In a second simulated use run, 3.774 grams of the solid product of this Example (Example 7) was added with gentle mixing to 200 ml of deionized water, having a pH of 6.5 and containing 5% by weight of dextrose, to determine if a "twice use concentrate" or stock solution (a solution having a concentration of dissolved solids which is twice as great as that of a solution used in hemodialysis or peritoneal dialysis) would be stable against calcium and magnesium carbonate precipitation. The pH of the solution after mixing was 7.7. After 72 hours sending, a slight film formed on the bottom of the test container, indicating the possibility of the formation of a small amount of precipitate. However, it is apparent that this concentrate (a stock solution which can be diluted with water to form a dialysis solution, said stock solution having twice use concentration of a dialysis solution) is commercially feasible using the product of Example 7.

In a third simulated use run, 5.661 grams of the product of this Example (Example 7) was added to 200 ml of deionized water of pH 6.5 to form a "concentrate" (a stock solution having three times the dissolved solids content of a dialysis solution). As in the second run, a faint film formed on the bottom of the test container, but the solution remained clear for 72 hours, after which precipitation was evident.

A fourth simulated use run used 7.548 grams of the solid product of this Example (Example 7) in 200 ml of deionized water having a pH of 6.5, to see if a "concentrate" (a stock solution having four times the dissolved solids content of a dialysis solution) could be prepared. A voluminous precipitate formed at once, indicating the precipitation of calcium carbonate and/or magnesium carbonate.

The foregoing solubility/stability runs were repeated using distilled water having a pH of 7 and solid product from Example 7. It was found that solutions of said product having a dissolved solids content suitable for use as dialysis solutions, with and without dextrose, could be prepared. These solutions had a pH of near 7.8 and were stable for over 48 hours after which precipitates formed. Stock solutions containing twice use concentrations (i.e., containing twice the amount of dissolved solids found in dialysis solutes) had a pH of 8.2 and a heavy precipitate of calcium carbonate and/or magnesium carbonate was formed after 48 hours. These experiments indicated that the small amount of acidity in the first used deionized water having a pH of 6.5 was an important factor in lowering the pH to slow down the formation of calcium carbonate and magnesium carbonate precipitates.

In hemodialysis and peritoneal dialysis practice, the diluted for use dialysate solution is adjusted to a pH of between 7.2 and 7.4, using a small amount of HCl or acetic acid if necessary, to assure compatibility with the blood. The pH of dialysis solutions and stock solutions, including those prepared from the sodium acetate system and the sodium bicarbonate systems of this invention can also be adjusted if necessary. However, it is preferred, when utilizing the sodium bicarbonate compositions of the first or second sodium bicarbonate systems of this invention, to adjust the pH of the water used to prepare dialysis solutions therefrom to about 6.4 prior to preparing the solutions to assure maintaining a pH in the range of 7.2 to 7.4 during the dilution process. This will mitigate against a basic environment in the solutions which would favor the formation and precipitation of calcium and magnesium carbonates.

EXAMPLE 8

(Thin Section Drying)

A dry dialysate product (a first sodium bicarbonate system of this invention) was made comprising bicarbonate, sodium, potassium, calcium, magnesium, chloride and acetate which, when added to the water at the rate of 9.2173 grams per liter, provides the following ion constituent concentrations:

| | |
|---|---|
| $Na^+$ | 134 mEq/l |
| $K^+$ | 2.5 mEq/l |
| $Ca^{++}$ | 2.5 mEq/l |
| $Mg^{++}$ | 1.5 mEq/l |
| $Cl^-$ | 101.5 mEq/l |
| Bicarbonate Ions | 35 mEq/l |
| Acetate Ions | 4 mEq/l |

The following weights of Reagent Grade anhydrous starting materials were used to prepare a sample sufficient to make ten liters of diluted-for-use dialysate solution (i.e., a solution suitable for use in hemodialysis or peritoneal dialysis):

| | |
|---|---|
| $NaHCO_3$ | 29.400 grams |
| $MgCl_2$ | 0.712 grams |
| $CaCl_2$ | 1.387 grams |
| KCl | 1.865 grams |
| Sodium Acetate | 3.279 grams |
| Sodium Chloride | 55.530 grams |
| | 92.173 grams total used |

$CaCl_2$ (1.387 grams), $MgCl_2$ (0.712 grams) and KCl (1.865 grams) were placed in a 9" diameter pyrex pie plate, to which was added 15 grams of water. The water totally dissolved the calcium, mangesium and potassium chlorides. NaCl (55.530 grams) was added to the solution in the dish and well mixed by a rubbing action with a spatula. Sodium acetate (3.279 grams) was added and mixing of the resulting semi-fluid mass, which contained some finely divided undissolved sodium chloride was continued until all components were thoroughly admixed in the hydrous media, as in Example 7. Then the water was evaporated as in Example 7.

Total water evaporation to constant weight was accomplished in less than four minutes in the above-described microwave oven at the "low heat" setting. Material (intermediate product) recovered weighed 62.77 grams, which was close to the theoretical value. The dried material was ground to pass a 20-mesh screen and 29.4 grams of finely divided (−60 +200 mesh) anhydrous sodium bicarbonate was admixed therewith to make the final solid product of this Example (Example 8), said final product being a composition of the first sodium bicarbonate system of this invention.

As taught in the discussion of Example 7, supra, the product of this Example (Example 8) was added to distilled water adjusted to a pH of 6.5 with acetic acid prior to use, in the amount required to prepare a solution suitable for use in hemodialysis or peritoneal dialysis. No evidence of magnesium carbonate or calcium carbonate precipitation was observed for over 72 hours.

EXAMPLE 9

(Thin Section Drying; Dextrose Added)

The procedure of Example 7 was repated. However, in this instance, the procedure was modified by adding finely divided (−20 mesh) anhydrous dextrose to the final sodium bicarbonate-containing product of said Example 7 and admixing the dextrose with said product. The dextrose was added in an amount to provide dextrose at the rate of 250 mEq/l of dialysate prepared from the dextrose-containing product or composition. Said dextrose-containing product was excellently adapted for preparing dialysis solutions.

EXAMPLE 10

(Thin Section Drying; Dextrose Added)

The procedure of Example 8 was repeated. However, in this instance, the procedure was modified by adding finely divided (−20 mesh) anhydrous dextrose to the final sodium bicarbonate-containing product of Example 8 and admixing the dextrose with said product to produce a composition of the first sodium bicarbonate system of this invention which contains dextrose and potassium chloride. The dextrose was added in an amount to provide 250 mEq of dextrose per liter of dialysis solution. The dextrose-containing composition wa excellently adapted for preparing dialysis solutions.

EXAMPLE 11

(Fluid Bed Drying with Recycle)

The dry, free-flowing, stable, non-caking dust-free granular products or compositions of the first sodium bicarbonate system of this invention can be prepared in a continuous manner by using the following procedure, which is designed to produce granular product. For convenience, materials used and produced are given on a basis of grams per ten liters of diluted product, i.e., on the basis of starting materials required to produce 10 liters of dialysis (hemodialysis or peritoneal dialysis) solution, as described in the foregoing Example 7.

Referring to FIG. 1: On a basis of materials required for ten liters of dialysis solution per hour: 1.941 grams of $CaCl_2$, 0.712 grams $MgCl_2$, 15 grams of $H_2O$, 59.034 grams of NaCl, 3.28 grams $CH_3COONa$ and no KCl are co-mingled in blender 1 to form a fluid pasty mass at a rate of 79.968 grams/hour. Said fluid pasty mass (79.968 grams/hour) is passed (e.g., by a conveyor belt, screw conveyor or the like) proportionally and in a continuous manner and at a rate of 79.968 grams/hour to first mixer 2, where it is intimately admixed with 64.968 grams/hour of ground or crushed oversize and fine recycle material from a later recited sizing (crushing and classifying) operation to form a granular particulate mass which is passed at the rate of 144.936 grams/hour to fluid bed dryer 3, where it is contacted with drying air having a flow rate and temperature effective for maintaining the temperature of the bed within fluid bed dryer 3 at about 130° C. Water is vaporized from the fluid bed at the rate of 15 grams/hour. Dry intermediate product from fluid bed dryer 3 is passed at the rate of 129.936 grams/hour to first crusher 4 where it is crushed. Crushed intermediate product (129.936 grams/hour) is passed from first crusher 4 to first classifier 5, from which 64.968 grams/hour of granular particles passing through a 20-mesh screen and retained on a 60-mesh screen are collected as intermediate product, and the particles (64.968 grams/hour) retained on a 20-mesh screen or passing a 60-mesh screen are recycled. Particles passing the 60-mesh screen are recycled directly to first mixer 2 while those retained on the 20-mesh screen are passed to second crusher 6 and from there to second classifier 7. Oversize particles (particles retained on a 60-mesh screen) are recycled from second classifier 7 to second crusher 6 while those passing through said 60-mesh screen are passed to first mixer 2 as recycle.

Figure 4:
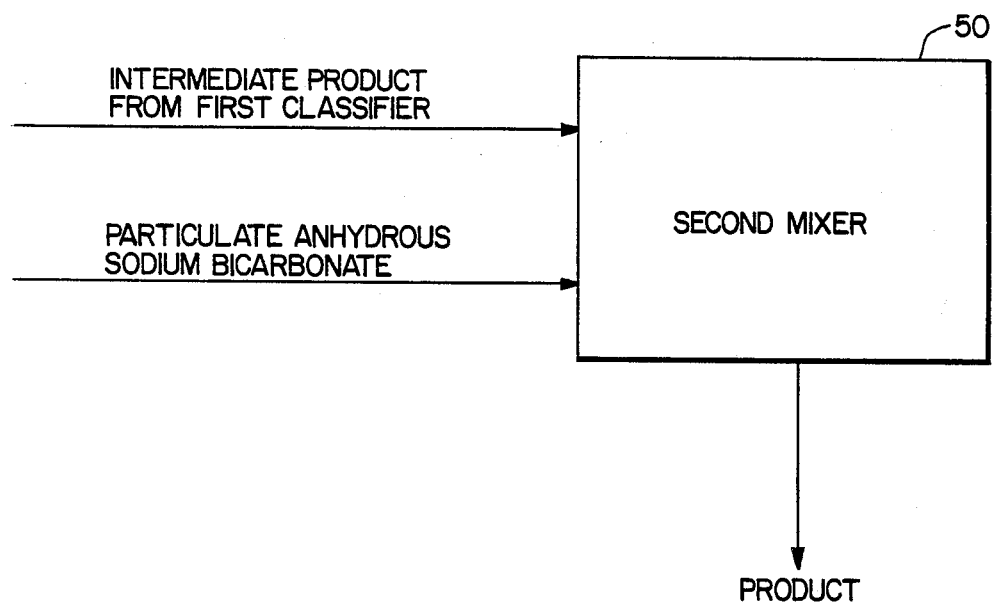
FIG. 4 is a flow-sheet illustrating the mixing of particulate sodium bicarbonate with sodium bicarbonate free granular intermediate product in the preparation of a solid product of the first sodium bicarbonate systems of the instant invention.

The 64.968 grams/hour of intermediate product from the first classifier is passed to second mixer 50 (FIG. 4) where it is co-mingled with 29.4 grams/hour of finely decided (−60 +200 mesh) anhydrous sodium bicarbonate to form a final product, a composition of the first sodium bicarbonate system of this invention. Said final product is useful for preparing dialysis solutions suitable for use in hemodialysis and peritoneal dialysis.

EXAMPLE 12

(Fluid Bed Drying with Recycle)

The dry, free-flowing, stable non-caking dust-free granular products or compositions of the first sodium bicarbonate system of this invention can also be prepared in a continuous manner by using the following procedure. As in Example 11, materials used and products pnxked are given in quantities required for 10 liters per hour of a dialysate (dialysis solution) which is ready for use:

Referring to FIG. 2: $CaCl_2$ (1.941 grams), $MgCl_2$ (0.713 grams), $H_2O$ (97.452 grams), NaCl (59.034 grams), $CH_3COONa$ (3.28 grams) and no KCl are mixed in a first mixer 10 to form, at a rate of 162.42 grams/hour, a concentrate (solution) having a 40% dissolved solids content. The resulting solution is preheated under pressure to about 130° C. (using any conventional indirect heating means, not shown) and introduced as a fine spray from nozzle 11 (e.g., a spray head nozzle such as a hollow-cone nozzle, a solid-cone nozzle, a fan nozzle, an impact nozzle, a rotating disc nozzle or the like) into fluid bed dryer 12 (where said solution is contacted with an air stream having a temperature and flow rate effective for maintaining a bed temperature of about 130° C.). Fluid bed dryer 12 contains a bed of previously prepared granules having a composition substantially the same as that obtained by vaporizing the water from said concentrate and having diameters of up to about 6.5 mm. The introduced solution is distributed over the surfaces of the granules within fluid bed dryer 12 which, as noted supra, has an internal temperature of about 130° C. The granules in the fluid bed dryer comprise a mixture of recycled intermediate product from a later recited sizing (crushing and classifying) step and resident granular material held in the bed for contact time purposes. Water is evaporated from the solution added to the fluid bed dryer at the rate of 97.452 grams/hour to yield 129.936 grams/hour of dried effluent. Said dried effluent is passed from fluid bed dryer 12 to first crusher 13 and from said first crusher to first classifier 14 at a rate of 129.936 grams/hour. Granular intermediate product passing a 20-mesh screen and retained on a 60-mesh screen is collected at the rate of 64.968 grams/hour while fines (particles passing a 60- mesh screen) and oversize particles (particles retained on a 20-mesh screen) totalling 64.968 grams/hour are used as recycle. The fines are passed from first classifier 14 to fluid bed dryer 12, while oversized material is passed from first classifier 14 to second crusher 15. The oversize material, after being crushed in second crusher 15, passes to second classifier 16 where it is classified. Oversize material from second classifier 16 (i.e., particles retained on a 60-mesh screen) are recycled to second crusher 15 while material passing through a 60-mesh screen is recycled to fluid bed dryer 12.

The 64.968 grams/hour of intermediate product from the first classifier is passed to second mixer 50 (FIG. 4) where it is co-mingled with 29.4 grams/hour of finely divided (31 60 +200 mesh) anhydrous sodium bicarbonate. The combined material comprises an example of a solid sodium bicarbonate system of this invention which is useful for preparing dialysis solutions suitable and useful for use in hemodialysis and peritoneal dialysis.

EXAMPLE 13

(Spray Drying with Recycle)

The dry, free-flowing, stable, non-caking, dust-free granular products or compositions of the first sodium bicarbonate system of this invention can be prepared in a continuous manner by using the following procedure. As in Example 11, materials used and product produced are given in amounts required for 10 liters per hour of dialysate (dialysis solution) which is ready for use.

Referring to FIG. 3: $CaCl_2$ (1.941 grams/hour), $MgCl_2$ (0.713 grams/hour), $H_2O$ (97.452 grams/hour), NaCl (59.034 grams/hour), $CH_3COONa$ (3.280 grams/hour) and no mixer 20 to prepare a 40% (solid content) concentrated feed solution in the amount of 162.42 grams/hour. This concentrated feed solution is preheated under pressure to about 150° C. (using any conventional indirect heating means not shown) and passed into spray dryer 21 in the form of small droplets from nozzle 27 (which can be a nozzle of the type described in Example 12, supra) where droplets are contacted with (a) a stream of heated drying air having a temperature and flow rate effective for forming a dry, granular intermediate product of this invention, and (b) a stream of 64.968 grams/hour of finely divided (−60 mesh) recycled material from a later recited sizing (crushing and classifying step).

Air exists from spray dryer 21 carrying with it 97.452 grams/hour of water and then passes through cyclone 22 before being vented to the atmosphere.

Dried intermediate product (129.936 grams/hour) exits from the lower section of spray dryer 21 in two portions—a first portion and a second portion. Said first portion passes directly from said spray dryer 21 to first crusher 23, while said second portion passes (with air exit spray dryer 21) to cyclone 22 where said second portion of dried intermediate product is collected and passed to first crusher 23. Crushed intermediate product from first crusher 23 passes to first classifier 24 at a rate of 129.936 grams/hour. Granular intermediate product from first crusher 23 passing a 20-mesh screen and retained on a 60-mesh screen is collected at the rate of 64.968 grams/hour while fines (particles passing a 60-mesh screen) and oversize particles (particles retained on a 20-mesh screen) totalling 64.968 grams/hour are used as recycle. Fines are passed from first classifier 24 to spray dryer 21, while oversize material is passed from first classifier 24 to second crusher 25. The oversize material, after being crushed in second crusher 25, passes to second classifier 26 where it is classified. Oversize material from second classifier 26 (i.e., particles retained on a 60-mesh screen) are recycled to second crusher 25 while material passing through the 60-mesh screen is recycled to spray dryer 21.

The 64.968 grams/hour of dry intermediate product from the first classifier is passed to second mixer 50 (FIG. 4) where it is co-mingled with 29.4 grams/hour of finely divided (−60 +200 mesh) anhydrous sodium bicarbonate. The combined material comprises an example of a product of this invention—a first sodium bicarbonate syste useful for preparing dialysis solutions suitable for use in hemodialysis and peritoneal dialysis.

When starting a run using the general procedures of Example 11, 12 or 13, finely divided (e.g., ca. −60 mesh) intermediate product from a previous run, if available, can be substituted for recycled material. If such intermediate product is not available, "substitute intermediate product" can be prepared by drying and then crushing and classifying an admixture of the solid starting materials or one of the solid starting materials—NaCl being a preferred material—but not including sodium bicarbonate. If desired, when using such substitute intermediate product, the process can be operated at substantially total recycle for about ½ hour before collecting intermediate product. Alternatively, a first portion (e.g., the first ½ hour's production) of intermediate product obtained where using such substitute intermediate product as simulated recycled material can be discarded.

When using the procedure of this Example (Example 13), fresh feed solution will tend to be distributed on the recycled particles in the spray dryer where it will tend to agglomerate said particles together during the drying operation to produce non-dusting intermediate product of this invention. Solid effluent temperature is preferably maintained between 120° and 130° C.

When using a spray dryer to prepare the granular intermediate product of this invention, a maximum inlet air temperature consistent with not over-heating the product is preferably used. The system within the spray dryer is cooled as water is vaporized therefrom. Thus, or energy efficient operation and desired product quality, an economic balance is sought and obtained as illustrated herein.

EXAMPLE 14

(Thin Section Drying; No Sodium Acetate Present)

This example illustrates the preparation of a composition of the first sodium carbonate syste of the instant invention which does not contain sodium acetate. Following the procedure outlined in Example 7, $CaCl_2$ (1.941 grams) and $MgCl_2$ (0.713 grams) were placed in a 9-inch diameter Pyrex pie plate to which was added 15 grams of water. The water totally dissolved the calcium and magnesium chlorides. NaCl (61.37 grams) was added to the solution in the dish. A gentle rubbing action with a spatula was sufficient to form a fluid mass, indicating that the magnesium and calcium chloride salts wer thoroughly intermixed with the dissolved sodium chloride and the few remaining small solid particles of sodium chloride. The fluid, semi-pasty mass was then spread uniformly in the pie plate and subjected to electromagnetic heating to rapidly remove the water present. Approximately 10 grams of water was evaporated in the first two minutes of heating.

After an additional two minutes of heating, it was found that the 15 grams of water added had been evaporated, and a mixed micro-particulate product formed. An additional two minutes of heating produced no further weight loss, indicating that the product was anhydrous as defined in this specification.

The 64.02 grams of material from the foregoing procedure was ground in a mortar to pass a 20-mesh screen and admixed with 29.4 grams of −60 +200 mesh anhydrous sodium bicarbonate to form 93.42 grams of granular acetate-free product of the first sodium bicarbonate system of this invention.

On a per liter of diluted for use basis, 9.342 grams of the product of this Example (Example 14) provides the ion concentrations commercially useful for dialysis (hemodialysis or peritoneal dialysis) purposes.

I do not wish to be bound by any theory to explain the unexpected resistance to calcium carbonate and magnesium carbonate precipitation exhibited by the first sodium bicarbonate system of this invention when dissolved in water to prepare solutions for use in hemodialysis or for peritoneal dialysis. It is evident, however, that the instantly disclosed means of distributing the magnesium and calcium salts over the surface of and through the relatively large quantity of sodium chloride, all in the final form of mixed micro-particles having rapid solubility properties in admixture with finely divided and readily soluble anhydrous sodium bicarbonate, provides a preferred means whereby stock solutions and dialysates can be prepared which avoid the possibility of having an appreciable localized concentration of calcium, magnesium and bicarbonate ions which is required to cause precipitation.

Example 15 illustrates the preparation of a composition of the second sodium bicarbonate system

EXAMPLE 15

This example demonstrates the feasibility of preparing a solid composition of the second sodium bicarbonate system of this invention by the simple admixture of finely divided anhydrous components. This is not a preferred procedure, but such dry products are useful for making reasonably stabledialysate solutions at use concentrations (i.e., having the concentration required for use in hemodialysis or peritoneal dialysis without further dilution).

As described in Example 7 materials used in this Example were dried to constant weight in a microwave oven to assure the absence of any water that would allow reaction between the calcium and magnesium chlorides and sodium bicarbonate.

Materials used in this Example are sufficient to prepare 10 liters of dialysis solution ready for use without further dilution. Finely divided (passing a 200-mesh U.S. standard screen) dry: (a) NaCl (59.034 grams), (b) $CH_3COONa$ (3.28 grams), $CaCl_2$ (1.941 grams), (d) $MgCl_2$ (0.713 grams), and (e) $NaHCO_3$ (29.40 grams) were placed in a dry, tightly stoppered 500 ml sample bottle and well mixed by repeated shaking. The solid product of this Example (Example 15) is a dry composition of the second bicarbonate system of the instant invention, but it is a less preferred product than the dry composition of the first sodium bicarbonate system of said invention.

As a use test of this material (the solid product of Example 15), 9.437 grams of said material was dissolved in one liter of distilled water (the pH of which was first adjusted to 6.5 by the addition of dilute acetic acid) to form a dialysate solution suitable for use without further dilution. The solution having a pH of 7.2 showed no precipitate for about 10 hours, after which a precipitate of calcium carbonate and magnesium carbonate was evident. A twice-use concentrate stock solution (prepared from said material) having such concentration that it could be diluted with an equal volume of water before use as a dialysis solution showed immediate evidence of carbonate precipitation.

In present day commercial dialysis practice (as illustrated by instructions for using the above-mentioned Renal Systems SB-600), the dialysate solution is adjusted to a pH of between 7.2 and 7.4 after preparation, using a small amount of acid if necessary to assure compatibility with blood. Diluted solutions of the instant invention should also be adjusted when required. However, in using dry dialysate products comprising sodium bicarbonate of this invention; it is preferred to adjust the pH of the water used to about 6.5 prior to use, to assure maintaining a pH in the range of 7.2 to 7.4 during the dilution process. This preferred procedure mitigates against possibly forming a basic solution environment of a pH over approximately 7.5, which favors the formation of calcium and magnesium carbonates.

The applicant cannot explain the capability of the products, as represented by the data given in Example 7, to form relatively stable, concentrated solutions. However, it is known that slight acidity, as provided by dilute acids or dissolved $CO_2$ and such salts as ammonium chloride, tend to increase the solubility of calcium and magnesium carbonates. It may be that presence of other salts comprising the product of said Example 7 also prevent nucleation and thereby retard the onset of precipitation.

In the development of the instant invention, the critical effect of pH, as it influences the onset of calcium and magnesium carbonate precipitation, was investigated using a sample of a composition prepared as described in Example 7. Solutions of twice use concentrations were used to study properties of the product. Table I describes materials used and observations made.

The series of solubility tests shown in Table I illustrate the critical nature of pH insofar as being important to the onset of calcium and magnesium carbonate precipitation from bicarbonate comprising dialysate solutions. At pH values in the vicinity of 7.5 and below, the solutions remain stable for several days. The required accepted use range pH of between 7.2 and 7.4 is thus met, using products of this invention.

TABLE I

| Run # | ml Distilled Water | ml 5% $CH_3COOH$ | Grams Product Used | pH of Solution | Remarks |
|---|---|---|---|---|---|
| 87-A | 200 | 0 | 3.774 | 7.9 | "Cloudy" on mixing. Heavy pcpt. in 24 hours |
| 87-B | 200 | 0.5 | 3.774 | 7.8 | "Clear" on mixing. Cloudy after 4 |

TABLE I-continued

| Run # | ml Distilled Water | ml 5% CH₃COOH | Grams Product Used | pH of Solution | Remarks |
|---|---|---|---|---|---|
| 87-C | 200 | 1.0 | 3.774 | 7.7 | hours; Pcpt after 24 hours "Clear" on mixing. Clear after 6 hours; Small amt. pcpt. after 24 hours |
| 87-D | 200 | 2.0 | 3.774 | 7.5 | "Clear" on mixing. Clear after 6 hours; Clear after 24 hours; Clear after 72 hours |
| 87-E | 200 | 4.0 | 3.774 | 7.2 | "Clear" on mixing. Clear after 6 hours; Clear after 72 hours |
| 87-F | 200 | 8.0 | 3.774 | 6.7 | "Clear" on mixing Clear after 6 hours; Clear after 74 hours |

In the course of work directed to developing an understanding of the importance of pH, when testing the product described in Example 15 (a composition of the second sodium bicarbonate system of this invention), there was observed what appeared to be a few small particles of undissolved magnesium and/or calcium chloride coated with magnesium and/or calcium carbonate. These were relatively large particles and not at all characteristic of the finely divided "cloudy" typical magnesium and calcium carbonate precipitates. If the pH of the particular sample was in the range of 7.2–7.4 and the solution was not more concentrated than use concentration, these particles would disappear in several hours, indicating that they dissolved slowly. It was also found that if a precipitate of calcium or magnesium carbonate formed, the addition of acid sufficient to lower the pH to the 7.2–7.4 range did not cause the precipitate to dissolve. This observation led the applicant to the conclusion that, with the bicarbonate systems of this invention, the pH of the water used should be adjusted, suitably with acetic acid, before use, to a value such that the final pH after mixing is in the 7.2–7.4 range. Conventional practice, as evidenced by Renal Systems SB-600 directions for use, calls for adjustment of pH after such mixing is accomplished.

In the sodium bicarbonate systems of this invention, the term "anhydrous" refers to a material state such that there is no water present that can take part in an aqueous phase reaction between $CaCl_2$ and $NaHCO_3$ or between $MgCl_2$ and $NaHCO_3$. In this work, it has been demonstrated that if a material is subjected to an R-F field (as in a microwave oven), water is readily vaporized and the material is rendered anhydrous as herein defined.

It has also been established that water of salt hydration is readily removed from compositions by radio frequency (R-F) energy. Traces of water that may remain after R-F heating are apparently not capable of causing reaction between calcium or magnesium salts and sodium bicarbonate. R-F heating is particularly applicable to preparation of sodium acetate and sodium bicarbonate systems of this invention.

It is also possible to produce substantially anhydrous NaCl, KCl, $MgCl_2$ and $CH_3COONa$ by other means of heating, such as spray drying and thin film surface heating above a hydrate's decomposition temperature, as taught in this specification, preferably using a sweep gas.

Control of pH and constituent concentrations at all times and in all portions of any solution comprising bicarbonate ions and calcium ions and/or magnesium ions is necessary. At a pH of slightly above 7.4, there is a great tendency for magnesium and calcium carbonates to precipitate. Considerably supersaturation is possible but apparently not universally reliable as evidenced by the published literature describing the problems of using sodium bicarbonate as alkalizing agent in dialysate products.

The screen size of granular product selected for use is a matter of convenience rather than one of necessity. For example, granular particles retained on a 20-mesh screen, but passing a 14 or 16 mesh screen could be used, except that it would take somewhat longer to dissolve them than it takes to dissolve granules passing a 20-mesh screen. Likewise, all granules passing, for example, a 14, 16, 20 or smaller (high sieve number) screen could be selected as product because they would dissolve quite rapidly, but fines (very fine particles therein) would produce some dusting when using the granules to prepare solutions. A body of very finely divided material (not in the preferred size range as herein described) tends to be more difficult to wet and dissolve than a granular material having the same chemical composition through which liquid can readily permeate. Thus, a minimum size, e.g., +60 mesh, +80 mesh or +100 mesh is generally selected for product particles (intermediate product particles in the case of a composition of the first sodium bicarbonate system of this invention. However, as noted supra, the choice of both minimum and maximum particle size is a matter of convenience rather than of necessity.

Solid particulate materials used or produced in the process of this invention can be conveyed by conveyor belts, screw conveyors, conveyor buckets, continuous flow conveyors, chain conveyors and the like.

Blenders (mixers) which are operable in the process of this invention (see, for example, the procedure described in Examples 4 and 11) include, but are not limited to, double cone blenders, twin shell vee-type blenders, revolving cone mixers and tumblers provided they are equipped with scrapers to prevent the build-up of material on their walls. Mixers which are operable in the process of this invention (see, for example, the procedure described in Example 4) also include, but are not limited to, blade mixers, rotor mixers, screw conveyor mixers, kneader mixers and ribbon mixers.

Crushers which are operable in the process of this invention (see, for example, the procedures described in Examples 4–6) include, but are not limited to, jaw crushers, gyratory crushers, cone crushers, pan crushers, roll crushers, rotary crushers, impact crushers, ball or pebble mill crushers and disc attrition mills.

Classifiers which are operable in the process of this invention (see, for example, the procedures set forth in Examples 4–6) include but are not limited to screens, including vibratory screens, sieves and air classifiers.

It should be noted that substantially any type of rapid drying device can be used to prepare the product of this invention providing the temperature is sufficiently low that the product is not decomposed or darkened.

A stream of drying gas (preferably heated) can be used to rapidly remove water from the material being dried. Pan granulators, rotary granulators and drum dryers are among the devices which can be used in preparation of products of this invention.

The specific operations conditions required for conducting the process used in preparing the granular product or granular intermediate product of this invention can vary widely, the principal requirement being that: (a) an intimate moist admixture of the constituents (ionic salts) is obtained before drying by co-mingling said constituents, except dextrose and sodium bicarbonate, (e.g., forming an aqueous solution or a dispersion of said constituents or by thoroughly admixing said constituents in finely divided form with at least one of said constituents being hydrated or partially hydrated or in solution, or at least a portion of at least one constituent being in solution, and (b) said intimate admixture is rapidly dried.

Vacuum or reduced pressure can be used in conjunction with heat to facilitate rapid removal of water. Also, a stream of heated air or other inert gas can be of value to facilitate the fast removal of water when using thin section drying or other drying methods.

Ease of water removal from any particle is greatly influenced by the particle size, shape and nature of the material being dried. The drying gas temperature, degree of saturation with water and method used to contact the drying gas with the particle being dried are important economic factors.

In the process of this invention, fluid bed drying and spray drying are particularly useful when product recycle is employed. One can advantageously use the available surface and particle heat content of the recycled material to obtain rapid heat transfer to the material being dried. The fresh feed to the process tends to be distributed in a thin section on the surface of the recycled material, thus obtaining rapid heat transfer from both the drying gas and from the recycled solids. Fresh feed (e.g., from a mixer as in the processes described in the procedures of Examples 5 and 6) may be distributed using spray nozzles or mechanically driven discs, wheels or the like.

Actual particle temperatures can only be estimated in processes that involve preheating of an aqueous feed under pressure to a temperature above the boiling point of water, followed by spray drying at atmospheric pressure. Particles issuing under pressure from a nozzle to atmospheric pressure cool rapidly because of water evaporation and almost instantaneously obtain a temperature near that of the ambient gas and any particles already in the chamber. These actions tend to cause rapid crystallization and favor formation of products having properties sought by this invention.

Process operating energy efficiency is commerically important but is not a limitation of the instant invention. The processes described in Examples 1–4, supra, require evaporation of water of salt hydration only, whereas the processes described in Examples 5–14 require evaporation of additional water used to dissolve and/or thoroughly disperse the salts involved.

In solutions used in hemodialysis or peritoneal dialysis, the concentrations of the various primary electrolytes are generally maintained near a constant level. However, these concentrations may be varied to meet the specific patient needs. For instance, some patients require special consideration regarding sodium and potassium levels.

Dextrose is frequently included in dialysis solutions. The dextrose concentration of such solutions may be varied from near zero to approximately 4.5%. Dextrose in solution may be handled separately in the dialysis procedure, or finely divided anhydrous dextrose may be admixed as required with products of this invention. For long package shelf-life, anhydrous dextrose is used in combination with the products of this invention. This specification is not meant to be limiting insofar as exactly how dextrose might be utilized with products of this invention. However, in the course of developing the compositions and products of this invention, it was observed that if even a small amount of dextrose is present during the drying step, this dextrose tends to undergo a browning reaction indicating decomposition. Thus, it is preferred to include dextrose as a separate entity if combined with the dry, granular products of this invention.

The term "dry" as applied to the granular product of this invention means that said product does not feel moist when pressed between one's fingers, that it is free-flowing and that it is substantially non-caking when packaged in a sealed, dry container or when stored in a dry atmosphere below the fusion point of the mixture for a prolonged period (e.g., six months or more).

The granular product of this invention is dust-free because tossing a 100 g portion of said product into the air (e.g., in a laboratory) does not produce a visible dust in said air.

The product granules of this invention are non-caking and free-flowing because a 250 g portion of said granules, after storing in a dry tightly closed 250 ml jar at 150° C. to 35° C. for three weeks, will flow from said jar in the form of discrete granules and not as chunks or lumps or aggregates of granules, when the jar is opened and inverted.

If, when operating processes using recycle, more than a predetermined amount of product size granules (e.g., −20, +60 mesh) is obtained per hour, such excess of product size granules can be passed, along with oversize granules from the first classifier to a crusher, classified and fine particles (e.g., −40, −60 mesh or −80 mesh) recycled to maintain a predetermined ratio of product to recycled material.

When starting a run using recycle and directed to the preparation of the sodium acetate system of this invention or to the first sodium carbonate system of said invention, finely divided (e g., ca. −60 mesh) product from a previous run, if available, can be substituted for recycled product material. If such product is not available, "substitute product" can be prepared by drying and then crushing and classifying an admixture of the solid starting materials (e.g., $CaCl_2$, $MgCl_2$, NaCl, $CH_3COONa.3H_2O$, etc.). If desired, when using such substitute product, the process can be operated at substantially total recycle for about ½ hour before collecting product. Alternatively, a first portion (e.g., the first ½ hour's production) of product obtained where using substitute product as recycled material can be discarded.

When using the procedure of Examples 6 and 13, fresh feed solution will tend to be distributed on the recycled particles in the spray dryer where it will tend to agglomerate said particles together during the drying operation to produce the non-dusting granules of this invention. Solid effluent temperature is preferably maintained between 120° and 130° C.

When using a spray dryer to prepare the granular product of this invention, a maximum inlet air temperature consistent with not over-heating the product is preferably used. The system within the spray dryer is cooled as water is vaporized therefrom. Thus, for energy efficient operation and desired product quality, an economic balance is sought and obtained as illustrated herein.

In the embodiments of Examples 6 and 13, recovery approaches 100% because a wet scrubber, not shown can (if desired) be used to recover fines (fine particles) in the air exit cyclone 22. Such fines can be used to prepare concentrated, feed solution in mixing tank 20.

When preparing a final product (i.e., a final composition of the first sodium bicarbonate system of this invention, a dry granular intermediate product or intermediate composition, which is described supra, is formed and mixed in a dry state with finely divided granular or particulate dry sodium bicarbonate to form the composition of said first sodium bicarbonate system. The dry granular intermediate product is of a size (e.g. −20 to +60 or −14 to +80, or −16 to +70 mesh, U.S. standard) which is effective for dissolving in water (after admixing with said finely divided granular or particulate dry sodium bicarbonate) to form a dialysis solution and which does not form substantial amounts of dust when handled in a dry state. The finely divided particulate dry sodium bicarbonate is of a size (e.g., −20 mesh, or −20 to +100 mesh or −30 mesh, or −60 to +200 mesh, or finer) which is effective for admixing with or coating over the dry granular intermediate product to form the final composition or product which is a composition of the first sodium bicarbonate system of this invention.

The dry, intimately mixed, chemically homogeneous granular compositions (or products) of the sodium acetate system of this invention are of a size (e.g. −20 to +60 mesh or −14 to +80 mesh) which is effective for dissolving in water to form dialysis solutions without forming substantial amounts of dust when handled in a dry state.

Recycled material (also called finely divided recycled particles) when preparing: (a) a composition of sodium acetate system of the instant invention, or (b) a composition of the first sodium bicarbonate system of said invention is of a size (e.g., −40 mesh or −60 mesh or −80 mesh or fines), which may tend to form dust when handled in a dry state and which is free of larger particles (e.g., particles larger than −40 mesh). The recycled material has the same composition as the final product when preparing a composition of the sodium acetate system of this invention. When preparing a composition of the first sodium bicarbonate system of this invention, the recycled material has the same composition as the intermediate product.

As used herein, "mesh" or "screen size" means U.S. standard and, unless otherwise defined where used, percent ("%") means parts per hundred by weight. As used herein, the term "R-F" means radio frequency.

As used in this specification, the terms "major" and "minor" amounts refer to the relative quantities of individual materials, for example, hemodialysis and peritoneal dialysis solutions as used normally contain minor amounts of potassium, calcium and magnesium ions. Namely, less than 5 mEq/l of solution, whereas sodium and chloride ions are present in major amounts of over 100 mEq/l of solution. Thus, a minor amount of potassium salt present in a granular composition (product) of this invention is an amount which will provide less than 5 mEq of potassium ion per liter of dialysis (hemodialysis or peritoneal dialysis) solution made from said granular composition.

Likewise, a minor amount of lactate ions or gluconate ions in a granular composition of this invention is an amount which will provide less than 5 mEq of such ions (lactate ions or gluconate ions) per liter of dialysis solution made from said granular composition.

A minor amount of sodium acetate in a granular composition of the first sodium bicarbonate system (or in a particulate composition of the second sodium bicarbonate system) of this invention is an amount such that a dialysis solution made from such granular composition of said first sodium bicarbonate system (or from such particulate composition of said second sodium bicarbonate system) will contain less than 5 mEq of sodium acetate (or acetate ions) per liter.

In the process as used to make granular products of this invention, two or more salts are dissolved or partially dissolved and the water is subsequently removed by evaporation. During the process, various anions and cations coexist in solution, for example, potassium ions, sodium ions, acetate ions and chloride ions. On evaporation of water to form anhydrous salts, there may be an exchange of anions and cations. For instance, if sodium acetate was used and if potassium chloride was used, on evaporation of water, some of the acetate may actually be present in the final product as potassium acetate. Such possible ion exchanges are believed to have little, if any, importance in conducting the processes of this invention or on the quality of the product obtained.

What is claimed:

1. A process for preparing a dry, free-flowing granular first composition suitable for preparing a hemodialysis solution and a peritoneal dialysis solution, said process comprising: (a) forming a dry granular second composition by dissolving salts consisting essentially of a major amount of sodium chloride and a minor amount of magnesium chloride and calcium chloride in water to form a process solution, rapidly vaporizing the water therefrom in the presence of finely divided recycled particles of the second composition to form a chemically homogeneous solid material consisting essentially of an intimate admixture of said salts and crushing the solid material to form the dry granular second composition and particles for recycling; and (b) mixing the granular second composition with finely divided anhydrous sodium bicarbonate to form said free-flowing granular first composition.

2. A process for preparing a dry, free-flowing, granular first composition suitable for preparing a hemodialysis solution and a peritoneal dialysis solution, said process comprising: (a) forming a granular second composition by dispersing comminuted salts consisting essentially of a major amount of sodium chloride and a minor amount of magnesium chloride and calcium chloride in an amount of water insufficient to dissolve all of said sodium chloride, rapidly vaporizing the water from the dispersion in the presence of recycled particulate second composition to form a chemically homogeneous solid material consisting essentially of an intimate admixture of said salts and crushing said solid material to form the granular second composition and particles for recycle; and (b) mixing the granular second composition with finely divided anhydrous sodium bicarbonate to form said dry, free-flowing granular first composition.

3. A process for preparing a dry, free-flowing granular first composition suitable for preparing a hemodialysis solution and a peritoneal dialysis solution, said process comprising: (a) forming a granular second composition by intimately admixing salts consisting essentially of a major amount of sodium chloride and a minor amount of magnesium chloride and calcium chloride to form an aqueous mass using, as a source of water, only water of hydration of the magnesium chloride and calcium chloride, and rapidly vaporizing the water from the aqueous mass to form a dry solid consisting of sodium chloride particles coated with dispersed magnesium chloride and calcium chloride, and crushing said dry solid to form the granular second composition; and (b) mixing the granular second composition with finely divided anhydrous sodium bicarbonate to form the dry, free-flowing, granular first composition.

4. The process of any one of claims 1, 2 or 3 in which the granular second composition contains at least one member selected from the group consisting of potassium ions, lactate ions, acetate ions and gluconate ions.

5. The process of any one of claims 1, 2 and 3 in which water is rapidly vaporized under reduced pressure.

6. The process of any one of claims 1, 2 and 3 in which the electromagnetic energy is used as the source of heat for vaporizing the water.

7. The process of any one of claims 1, 2 and 3 in which the electromagnetic energy is used as the source of heat for vaporizing the water and the water is vaporized under reduced pressure.

* * * * *